US009848949B2

(12) United States Patent
Osypka

(10) Patent No.: US 9,848,949 B2
(45) Date of Patent: Dec. 26, 2017

(54) RENAL DENERVATION SYSTEM

(71) Applicant: Oscor Inc., Palm Harbor, FL (US)

(72) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 478 days.

(21) Appl. No.: 14/295,765

(22) Filed: Jun. 4, 2014

(65) Prior Publication Data
US 2015/0201997 A1 Jul. 23, 2015

Related U.S. Application Data

(60) Provisional application No. 61/929,741, filed on Jan. 21, 2014.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/0022* (2013.01); *A61B 2018/00214* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00702* (2013.01); *A61B 2018/00714* (2013.01); *A61B 2018/00791* (2013.01); *A61B 2018/00821* (2013.01); *A61B 2018/00839* (2013.01);
(Continued)

(58) Field of Classification Search
CPC ............... A61B 18/14; A61B 18/1492; A61B 2018/0016; A61B 2018/00214; A61B 2018/0022; A61B 2018/00267; A61B 2018/00404; A61B 2018/00434; A61B 2018/00511; A61B 2018/00577; A61B 2018/00642; A61B 2018/00702; A61B 2018/00714; A61B 2018/00791; A61B 2018/00821; A61B 2018/00839; A61B 2018/1435; A61B 2018/1467; A61B 2018/1497
USPC ...................................... 606/41–50; 600/374
See application file for complete search history.

(56) References Cited

U.S. PATENT DOCUMENTS 5,730,704 A * 3/1998 Avitall ............... A61B 5/04085
600/374
6,152,920 A * 11/2000 Thompson ......... A61B 18/1492
600/374

(Continued)

*Primary Examiner* — Michael Peffley
*Assistant Examiner* — Khadijeh Vahdat
(74) *Attorney, Agent, or Firm* — Locke Lord LLP; Scott D. Wofsy

(57) ABSTRACT

A system for use in a renal denervation procedure includes a catheter having proximal and distal end portions, a sensor configured to sense a condition of one or more nerves, the sensor operatively associated with the distal end portion of the catheter, and at least one electrode disposed on the distal end portion of the catheter for delivering energy to renal tissue. A catheter includes a catheter body defining a distal end portion and a proximal end portion, and a sensor for sensing a renal sympathetic nerve, the sensor disposed on the distal end portion of the catheter body, wherein the sensor is configured to sense an electromagnetic signal from the renal sympathetic nerve.

7 Claims, 8 Drawing Sheets

(52) U.S. Cl.
CPC ......... *A61B 2018/1435* (2013.01); *A61B 2018/1467* (2013.01); *A61B 2018/1497* (2013.01)

(56) References Cited

U.S. PATENT DOCUMENTS

| | | | |
|---|---|---|---|
| 2008/0281312 A1* | 11/2008 | Werneth | A61B 18/1492 606/33 |
| 2013/0289369 A1* | 10/2013 | Margolis | A61B 5/01 600/309 |

* cited by examiner

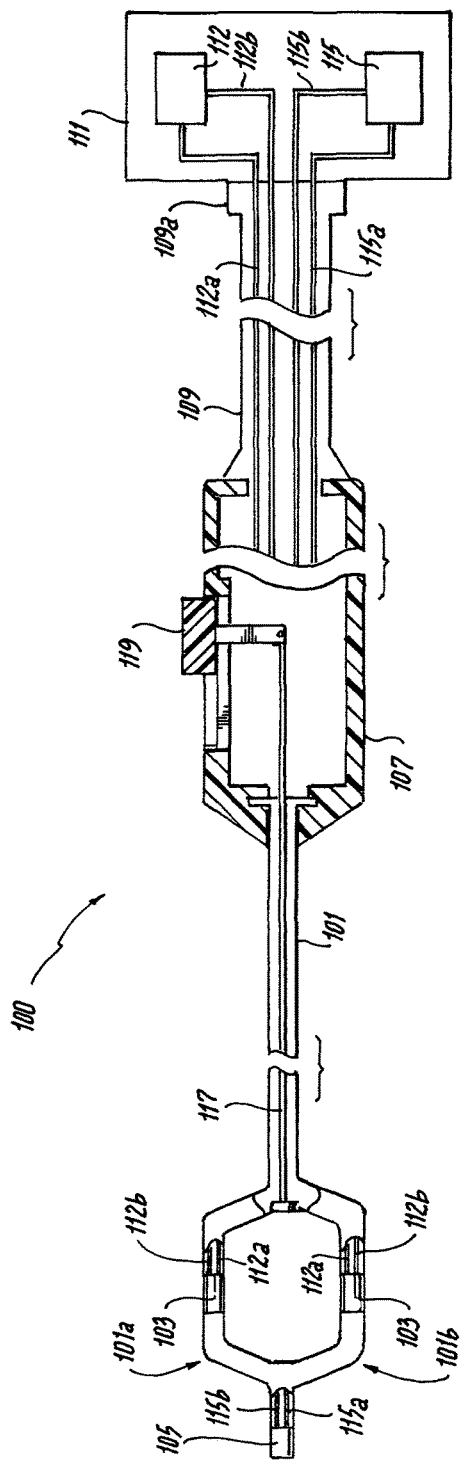
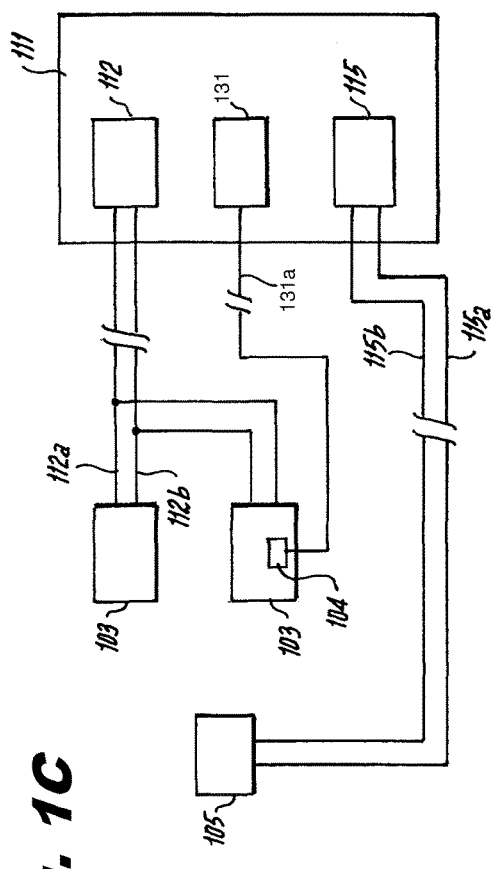
Fig. 1B
Fig. 1C

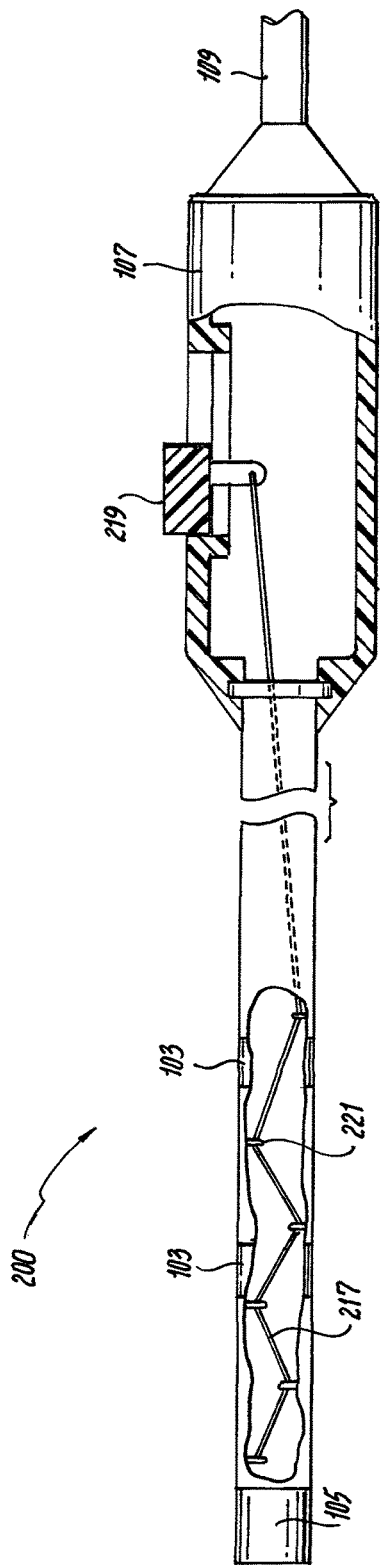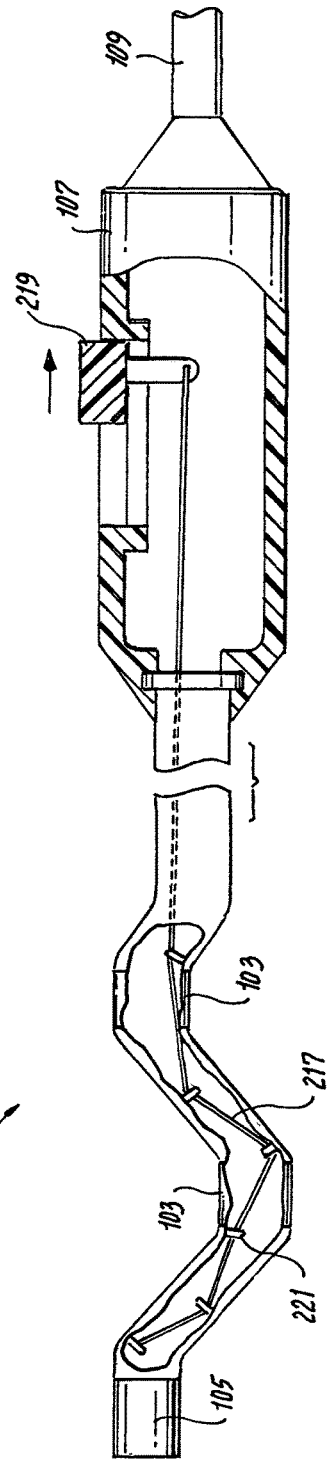
Fig. 2B
Fig. 2C

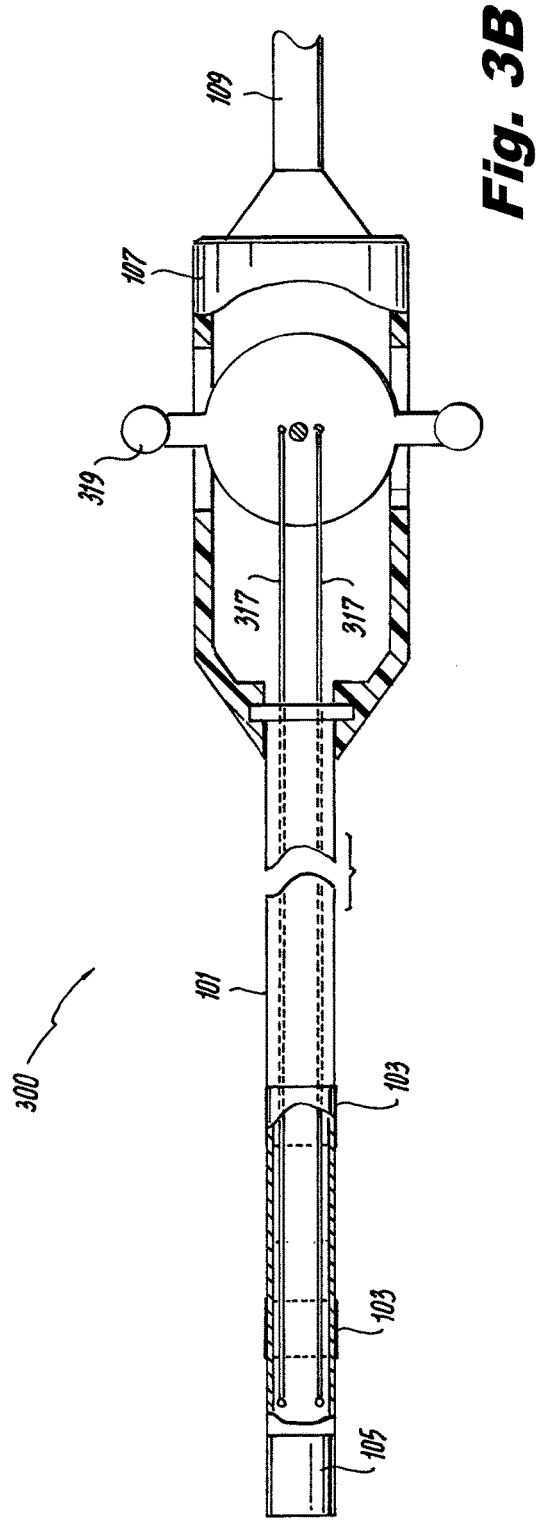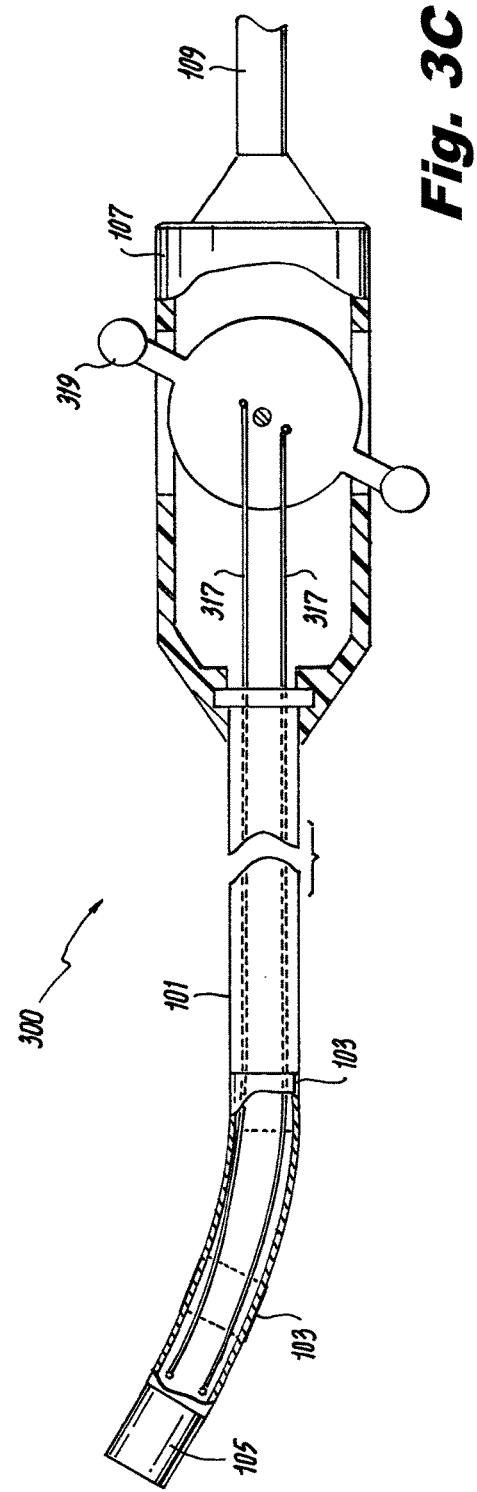

RENAL DENERVATION SYSTEM

CROSS REFERENCE TO RELATED APPLICATIONS

This application claims the benefit of and priority to U.S. Provisional Patent Application Ser. No. 61/929,741, filed Jan. 21, 2014, the disclosure of which is incorporated by reference herein in its entirety.

BACKGROUND OF THE INVENTION

1. Field of the Invention

The subject disclosure relates to ablation catheters, and more particularly, to ablation catheters for performing renal denervation procedures through the renal artery of a patient.

2. Description of Related Art

Renal denervation (RDN) is a procedure performed by interventional radiologists for the purpose of lowering the blood pressure of a patient. Renal denervation is a minimally invasive, endovascular catheter-based procedure using radiofrequency (RF) ablation aimed at treating resistant hypertension.

By applying RF pulses to the renal arteries, the nerves in the vascular wall (adventitia layer) can be denervated. This causes reduction of renal sympathetic afferent and efferent activity which in turn can decrease blood pressure. Early data from international clinical trials demonstrates average blood pressure reduction of approximately 30 mm Hg at three-year follow-ups in patients with treatment-resistant hypertension.

A common way to perform renal ablation is to ablate the renal artery by either heating tissue through radiofrequency or microwave ablation, irrigated heat ablation, and/or cryogenic ablation. It is believed that renal denervation works because it reduces the over-activity of the sympathetic nerve.

Ablation of the renal artery is commonly performed by gaining access through the femoral vein. However, in certain cases, this can cause substantial bleeding. Other options include access through the radial artery. But this method limits the use of catheter systems of 5F (French size) or smaller.

Current ablation catheters that are available to the market include: 1) single polar catheters offered by Medtronic of 710 Medtronic Parkway, Minneapolis, Minn., 55432-5604, which take substantial time to perform effective ablation of the renal artery; 2) cage form catheters offered by St. Jude Medical of One St. Jude Medical Drive, St. Paul, Minn., 55117-9983, which have several electrodes configured in a cage form; and 3) multiple ablation electrodes configured on an inflatable balloon, like those offered by Boston Scientific of One Boston Scientific Place, Natick, Mass., 01760-1537.

All multi-electrode systems have a common disadvantage. They are relatively bulky and large in diameter (7F or larger) and difficult to position into the renal artery, requiring a fixed curve or steerable guiding sheath. The combination of the larger catheter diameter plus the use of a larger guiding catheter often results in an effective system outer diameter of 8F or larger. Such large diameters are not desirable for femoral placement, as it can cause bleeding and result in lengthy recovery periods for the patient.

Another shortcoming of current renal denervation systems is that even though the physician can observe the positioning of the ablation catheter in the renal artery through contrast media supported X-ray, the physician does not know the location of the sympathetic nerves of the renal artery and therefore does not know the correct and ideal position of the catheter to be placed to make the actual ablation and treatment time as short and efficient as possible. Physicians are essentially performing this procedure blind, with presently available devices and the only indication available to a physician to indicate burning of the nerves is the patient exhibiting pain. Even though it is believed that the over-activity of the sympathetic nerves are responsible for higher blood pressure in a patient, the actual place or location of the nerve is not as important as seeing if the patient has an overactive sympathetic nerve signal.

Conventional ablation methods and systems have generally been considered satisfactory for their intended purpose. However, there is still a need in the art for improved catheter-based ablation systems. There also remains a need in the art for a system that is easy to make and use. The present disclosure provides a solution for these problems.

SUMMARY OF THE DISCLOSURE

In accordance with at least one aspect of this disclosure, a system for use in a renal denervation procedure includes a catheter having proximal and distal end portions, a sensor configured to sense a condition of one or more nerves, the sensor operatively associated with the distal end portion of the catheter, and at least one electrode disposed on the distal end portion of the catheter for delivering energy to renal tissue.

The at least one electrode can further include a plurality of axially spaced apart electrodes along the distal end portion of the catheter.

The system can further include a catheter handle at the proximal end portion of the catheter wherein the handle is connectable to a generator that is configured to provide energy to the at least one electrode for ablation of the renal artery.

The catheter handle can include an actuation portion for facilitating bidirectional steering of the distal end portion of the catheter within the renal artery. An overall diameter of the catheter can be less than about 5F (French size).

The distal end portion of the catheter can have a generally S-shaped configuration. In some embodiments, the distal end portion of the catheter has a generally spiral shaped configuration.

The at least one thermocouple can be disposed on the distal end portion of the catheter for regulating temperature of the plurality of electrodes during controlled ablation.

The system can further include a radio frequency generator operatively connected to the catheter handle to provide energy to the plurality of electrodes for ablation of the renal artery. The radio frequency generator can further include a sensing module for receiving a signal from the sensor and determining a level of activity of one or more nerves.

In at least one aspect of this disclosure, a method includes the steps of inserting the catheter into a renal artery and sensing a condition associated with a nerve of a renal artery using a sensor disposed on the catheter. The method can further include determining whether to ablate tissue based the sensed condition of the nerves. The method can further include ablating tissue if the nerves are sensed to be overactive.

In some embodiments, the method can further include controlling the temperature of the distal end portion during the ablation process through at least one thermocouple disposed thereon. The method can further include controlling an amount of energy applied to renal artery tissue based on a sensed condition of the nerves.

In at least one aspect of this disclosure, a catheter includes a catheter body defining a distal end portion and a proximal end portion, and a sensor for sensing a renal sympathetic nerve, the sensor disposed on the distal end portion of the catheter body, wherein the sensor is configured to sense an electromagnetic signal from the renal sympathetic nerve. The catheter can further include at least one electrode configured to electrically connect to an electro surgical energy source. In some embodiments, the catheter can further include a temperature sensor disposed thereon for sensing a temperature proximate a renal sympathetic nerve. A diameter of the catheter body is less than about 5F.

The catheter can further include a catheter handle at a proximal end portion of the catheter body wherein the handle is connectable to a generator that is configured to provide energy to the at least one electrode for ablation of a renal artery. The catheter handle can include an actuation portion for steering the distal end portion of the catheter body within the renal artery.

The distal end portion of the catheter body can have a generally S-shaped configuration. In some embodiments, the distal end portion of the catheter body can have a generally spiral-shaped configuration. The distal end portion of the catheter body can have a generally basket-shaped configuration. In some embodiments, the distal end portion of the catheter body can have a generally balloon-shaped configuration.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 1B is a cross-sectional view of the renal denervation system of FIG. 1A, showing an embodiment of the biasing mechanics and electrical connections to the generator schematically drawn;

FIG. 1C is schematic illustration of a circuit of the system of FIG. 1A, also showing a thermocouple operatively connected to one of the electrodes;

FIG. 2B is a cross-sectional view of the renal denervation system of FIG. 2A, showing the catheter in a straight condition;

FIG. 2C is a cross-sectional view of the renal denervation system of FIG. 2A, showing the catheter in a substantially S-shape condition;

FIG. 3B is a cross-sectional view of the renal denervation system of FIG. 3A, showing the catheter in a straight condition;

FIG. 3C is a cross-sectional view of the renal denervation system of FIG. 3A, showing the catheter in a steered and partially spiraled condition;

DETAILED DESCRIPTION OF THE INVENTION

Figure 1A:
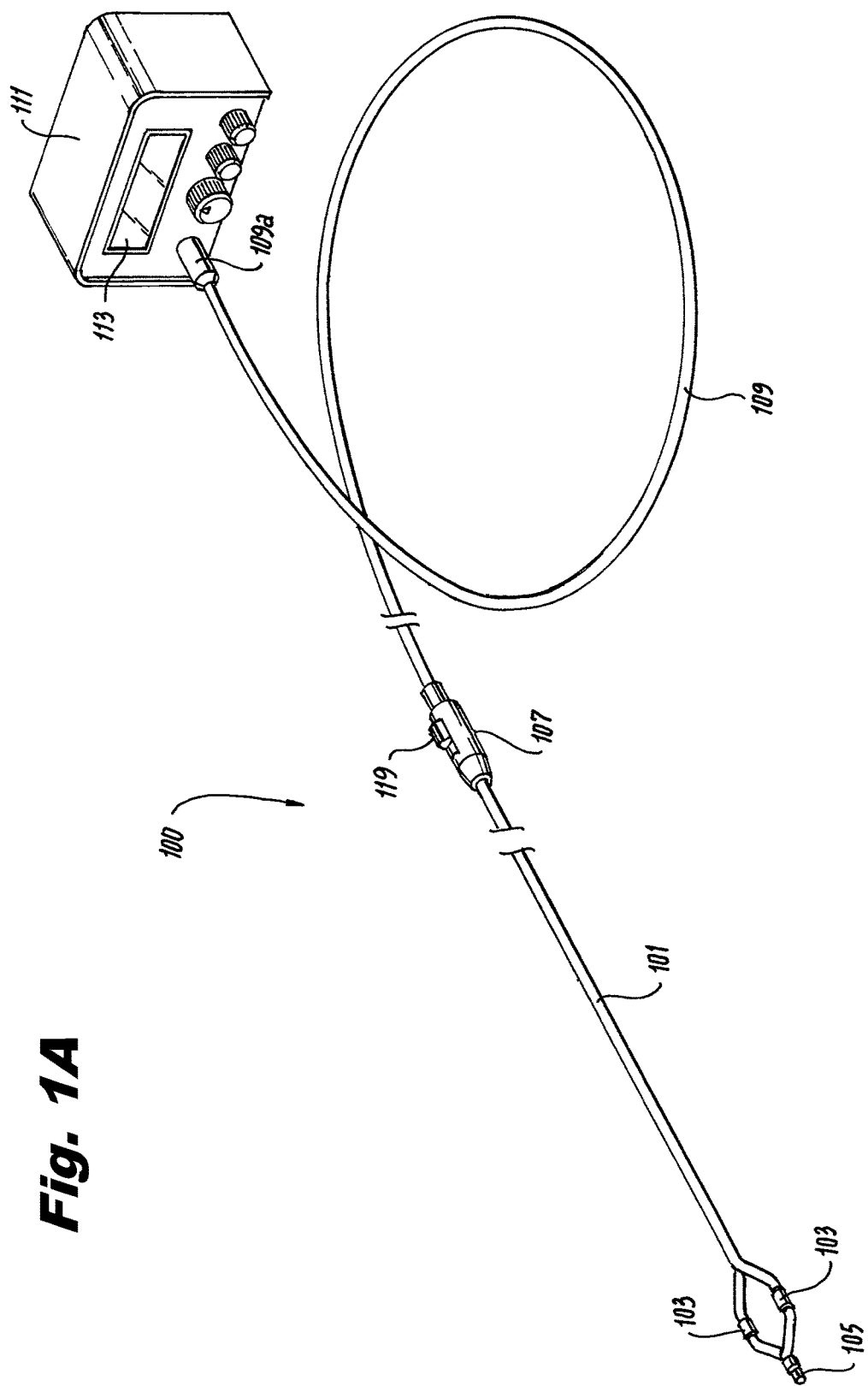
FIG. 1A is a perspective view of a renal denervation system of the present disclosure, with the distal end portion thereof biased in a basket shape condition.

Referring now to the drawings wherein like reference numerals identify similar features or structures of the disclosed invention, there is illustrated in FIGS. 1A-1C an embodiment of a renal denervation system constructed in accordance with a the subject disclosure and designated generally by reference numeral 100. More particularly, the system 100 is adapted and configured for ablating the interior walls of the renal artery to reduce renal sympathetic afferent and efferent activity, among other things. Other embodiments are shown in FIGS. 2A-5.

Referring to FIGS. 1A-1C, a renal denervation system 100 can be configured to perform ablation using electrosurgical energy from a generator 111 and/or any other suitable source of energy. It is also contemplated the renal denervation system 100 can be embodied using non-electrosurgical ablative means (e.g., cryogenics) configured to ablate the renal artery and/or sympathetic nerves associated therewith.

The system 100 includes at least one sensor 105 incorporated at a tip of the catheter body 101 that is configured to sense a condition of one or more nerves of a renal artery (e.g. to sense activity of sympathetic nerves of a renal artery). For example, the sensor 105 can be configured to sense electrical activity within a renal sympathetic nerve cell (e.g., via electromagnetic radiation given off by the nerve cell) and output a commensurate electrical signal. While the sensor is shown as disposed on the distal end of the catheter body 101, one or more sensors 105 can alternatively or conjunctively be disposed on any suitable portion of a distal portion of the catheter body 101.

Catheter body 101 can be of any suitable size such as, but not limited to, a small size micro-catheter. In some embodiments, catheter body 101 can include a diameter from about 0.5F to about 7F. In some embodiments, the diameter of the catheter is less than 6F. In some embodiments, the diameter of the catheter is about 5F, about 4F, about 3F, about 2F, or about 1F. The catheter body 101 can be made using any suitable materials such as, but not limited to, a biocompatible plastic, a shape memory material, a biocompatible metal, or combinations thereof. In some embodiments, the catheter body 101 includes coextruded polymer tubing. In other embodiments, the catheter body 101 includes single extrusion tubing defining one or more passageways for wires, mechanics, or the like.

Catheter body 101 can be connected to a handle 107 of any suitable shape and design. The handle 107 can be made of any suitable material or combination of materials (e.g., biocompatible plastic, metal, or the like). The handle 107 can be connected to a cable 109 which is configured to electrically connect to the generator 111 via a connector 109a. The handle 107 can include any suitable electrosurgical controls for selectively delivering electrosurgical energy to one or more of the electrodes 103. In some embodiments, electrosurgical controls may be present on the generator 111.

One or more electrodes 103 can be included on any suitable portion of catheter body 101 (e.g., near the distal end as shown). The electrodes 103 can be made of any suitable material such as, but not limited to, a conductive biocompatible metal. The system 100 can also be configured to perform temperature controlled ablation such that the system 100 can sense a temperature at any suitable portion of the catheter body 101 (e.g., at one or more electrodes 103) and modify an output of electrosurgical energy from the electrosurgical generator 111 based on the temperature of the electrodes and/or tissue.

In such an embodiment, the generator 111 can determine temperature using any suitable method (e.g., impedance change in tissue, thermal energy sensing at or near the tissue location). For example, one or more of the electrodes 103 can include a temperature sensor (e.g. a thermistor or a thermocouple) connected thereto and/or embedded therein for determining the temperature at a desired location for closed loop temperature control during an ablation procedure.

Referring to FIGS. 1B and 1C, each electrode 103 and/or temperature sensor 104 therein can be electrically connected to a connector 109a on cable 109 that is configured to connect to the generator 111 such that electrical signals can travel from the generator to the electrodes 103 and/or the temperature sensor 104. For example, wires 112a, 112b electrically connect the electrodes 103 to an electrosurgical module 112 in the generator 111 for selective delivery of electrosurgical energy to the electrodes 103. While each electrode 103 is shown as having two wires 112a, 112b, it is contemplated that electrodes 103 can be antennas and thus only use a single wire and/or any other suitable combination of wires. One having skill in the art would also appreciate that the connector 109a can be included on the handle portion 107 such that a cable connected to the generator 111 can connect removably to the handle 107.

The at least one sensor 105 can also be electrically connected to the connector 109a such that the generator 111 (and/or another suitable device) can receive signals from the sensor 105 to determine an activity and/or location of a renal sympathetic nerve. For example, wires 115a, 115b are shown connecting the sensor 105 to a sensing module 115 of the generator 111 for sensing an activity of a sympathetic nerve. The sensing module 115 of the generator 111 can include at least one of an electrical/mechanical circuit of any suitable design, a suitable software, or any other suitable device configured to receive electrical and/or digital signals from sensor 105 and to process the signals in a desired manner.

The sensor 105 can be used to sense biomedical signals such as electrical amplitudes, electric fields, magnetic fields, and/or electrical potentials caused by sympathetic nerve activity located outside the renal artery. The sympathetic nerve sends and/or receive electrical signals which can be identified as nerve activity. The electrical signals are very small and in the area of milli-($10^{-3}$) and/or micro-($10^{-6}$) Volts. Distinguishing sympathetic nerve bursts versus background or artifact-related noise can be a challenge. To account for this, the sensing module 115 can further include a filter module to filter out the surrounding noise.

The sensing module 115 can further indicate a condition associated with a sympathetic nerve based on the received signals. While the sensing module 115 is shown as included in the generator 111, one ordinarily skilled in the art would appreciate that the sensing module 115 can be external to the generator 111 such that the sensing module 115 is included in a separate device. In some embodiments, the sensing module 115 can be operatively associated with the handle 107 such that an indication of nerve activity and/or proximity can be displayed on the handle 107 or catheter body 101.

In at least some embodiments, the catheter body 101 and/or the distal end thereof can be flexible, steerable, or otherwise deformable in any suitable manner. Also, the distal end of the catheter body 101 can have any suitable configuration or shape in one or more states. The handle 107 can include controls (e.g., a button, switch, or other suitable device) for modifying the state of the distal end of the catheter body 101. Also, the catheter body 101 can be associated with a removable guiding sheath (not shown) for steering the catheter body 101 where the catheter body 101 itself is not configured to steer.

For example, as shown the embodiment of FIGS. 1A and 1B, the renal denervation system 100 can include a basket-shaped distal tip which can be flexed and/or deformed from a linear condition to the basket-shaped condition using any suitable device or means. For example, such a state change can be accomplished any suitable manner, such as, but not limited to, using biased arms contained by a sheath, shape memory materials activated by electricity or heat, mechanical shape changing devices, combinations thereof). In some embodiments, as shown in FIG. 1B, an actuating rod 117 extends through the catheter body 101 and is connected to a sliding switch 119 on the housing 107 to provide a biasing force to the distal end of the catheter body 101 such that the catheter body 101 transitions from a linear shape to the basket shape. As shown, the rod 117 is attached to a portion of the catheter body 101 near the basket shape and can pull on the catheter body 101 to separate arms 101a and 101b of the basket shape portion of the catheter body 101. In other embodiments, the catheter body 101 can include one or more of, e.g., a shape-memory material (e.g., Nitinol), a removable sheath, or a stylet configured to cause the catheter body 101 to transition between a linear state and the basket shape. Any other suitable means for creating the basket shape is contemplated herein.

Figure 2A:
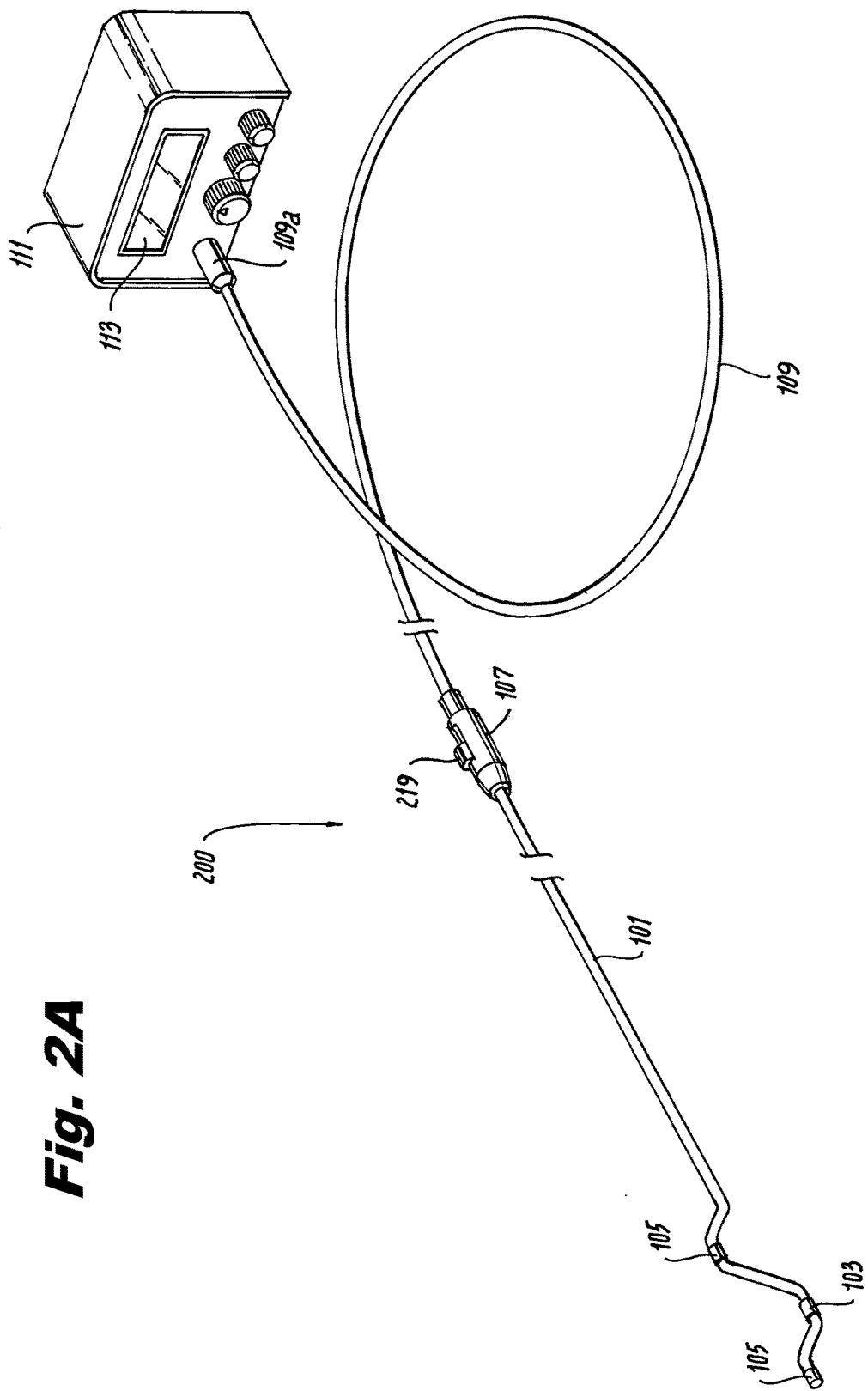
FIG. 2A is a perspective view of a renal denervation system of the present disclosure, with the distal end portion thereof arranged in an S-shape.

In another embodiment shown in FIGS. 2A-2C, a renal denervation system 200 is shown that is similar to system 100 described above, except that the distal tip includes is configured to be in an S-shape or wave-shape. For example, at least one control wire 217 can be disposed in the catheter body 101 and can be slidably attached to one or more anchors 221. The control wire 217 can be connected to a switch 219 for deforming the catheter body 101 from a substantially linear state (e.g., FIG. 2B) to an S-shape or wave-shape (e.g., FIG. 2C). In other embodiments, the catheter body 101 can include one or more of, e.g., a shape-memory material (e.g., Nitinol), a removable sheath, or a stylet configured to cause the catheter body 101 to transition from a linear state to an S-shape. Any other suitable means for creating the S-shape is contemplated herein.

Figure 3A:
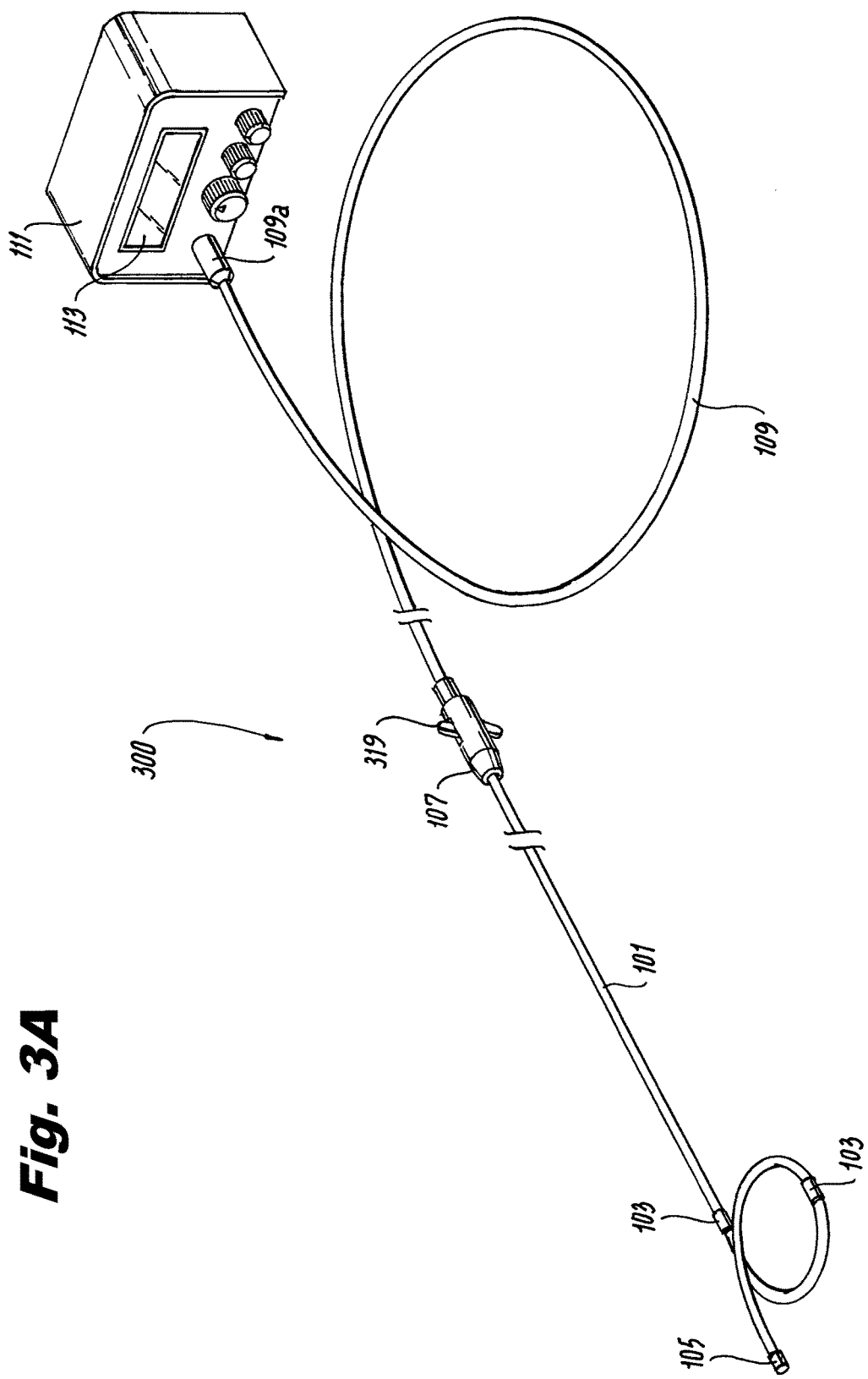
FIG. 3A is a perspective view of a renal denervation system of the present disclosure, with the distal end portion thereof arranged in a spiral shape.

In another embodiment shown in FIGS. 3A-3C, a renal denervation system 300 is shown that is similar to system 100 described above, except that the distal tip includes is configured to except that the distal tip of the catheter body 101 includes a spiral and/or steerable shape. For example, at least one control wire 317 can be disposed in and connected to the catheter body 101. The control wire 317 can be connected to a steering control 319 for deforming the catheter body 101 from a substantially linear state (e.g., FIG.

3B) to an at least partially spiral or bent shape (e.g., FIG. 3C). In other embodiments, the catheter body 101 can include one or more of, e.g., a shape-memory material (e.g., Nitinol), a removable sheath covering a material biased to spiral, or a stylet configured to cause the catheter body 101 to transition between a linear state and the spiral/steered shape. Any other suitable means for creating the spiral shape is contemplated herein.

Figure 4:
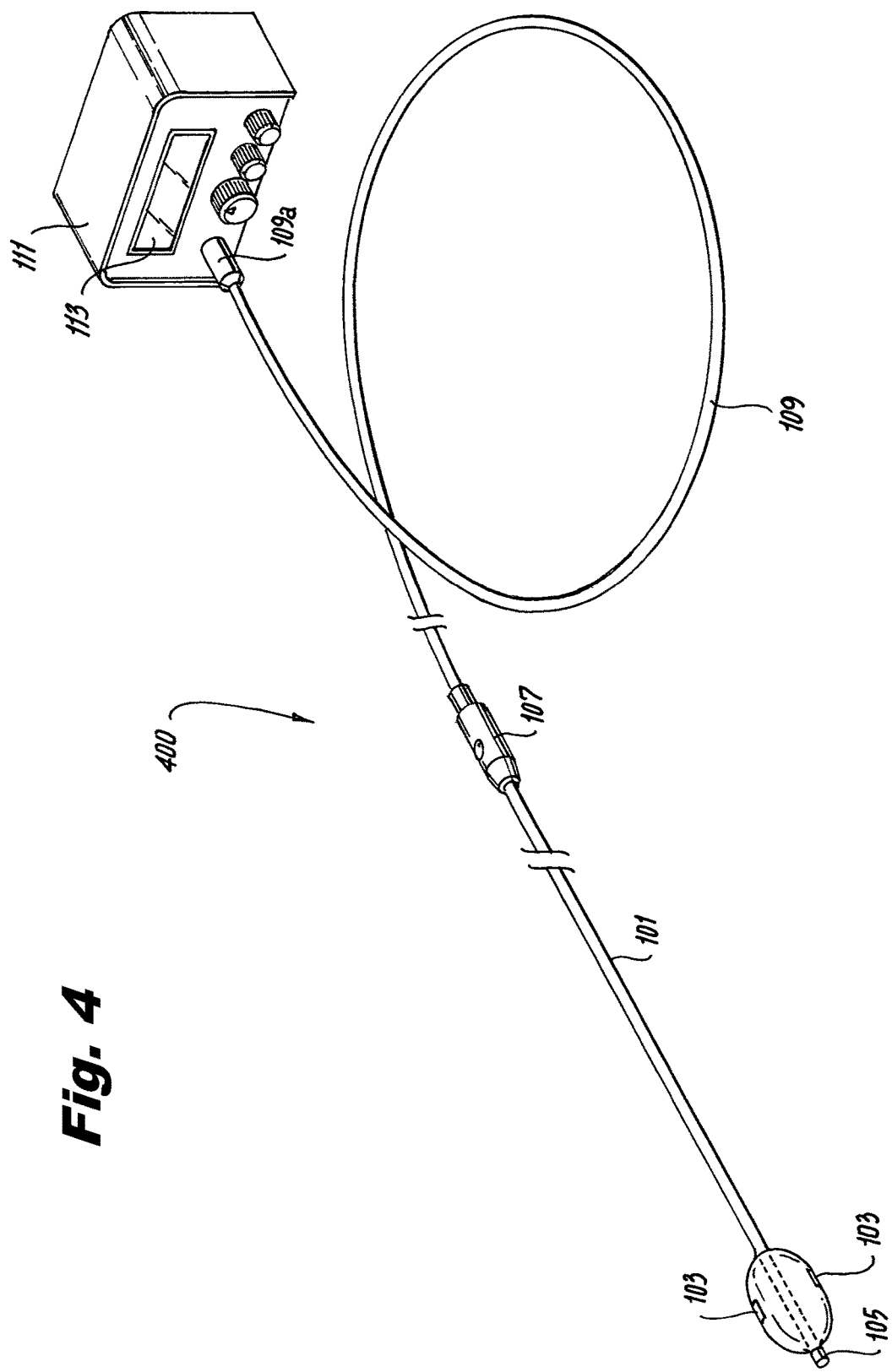
FIG. 4 is a perspective view of a renal denervation system of the present disclosure, with the distal end portion thereof arranged in a balloon shape, showing the balloon inflated.

In accordance with another embodiment, FIG. 4 depicts a renal denervation system 400 similar to system 100 described herein, except that the distal tip of the catheter body 101 includes an inflatable and/or deflatable balloon 417. The catheter body 101 can be transitioned between a first state (e.g. a linear state) to a second state (e.g. the non-linear and/or expanded states as shown in FIG. 4) via any suitable means, such as, but not limited to, by pumping a gas or other fluid into the balloon 417 and/or mechanically expanding balloon 417. In other embodiments, the catheter body 101 can include one or more of, e.g., a shape-memory material (e.g., Nitinol), a removable sheath covering a biased balloon shaped material, or a stylet configured to cause the catheter body 101 to transition from a linear state to the spiral or steered shape. Any other suitable means for expanding the balloon 417 is contemplated herein.

Generator 111 (e.g., an RF ablation generator) can be any suitable electrosurgical generator configured to output electrosurgical energy (e.g., RF, MW, etc.). Generator 111 can include a single or multi-channel configuration, and can further have a close loop temperature control to perform temperature controlled RF ablation using one or more temperature sensors 104 associated with electrodes 103 as described above. The temperature sensors 104 can be connected to a temperature sensing module 131 as described above with reference to FIG. 1C. Also, any suitable indicator (e.g., visual, auditory, tactile) can be operatively connected to the temperature sensing module 131 to indicate a high, low, suitable, or numeric temperature.

Additionally, the generator 111 can include a sensing module 115, as described above, configured to receive signals from the sensor 105 for sensing a condition of a renal sympathetic nerve. The sensing module 115 can be configured to convert electrical signals into information regarding the activity (e.g., electrical activity, patterns of electrical activity) of the renal sympathetic nerves. Also, any suitable indicator (e.g., visual, auditory, tactile) can be operatively connected to the sensing module 115 to indicate a particular activity or state of the sensed nerves (e.g., cell over activity, cell underactivity, proper ablation achieved).

Any other suitable measuring and/or control systems can be included in the generator 111. For example, such measuring and control systems can be implemented via any suitable electrical hardware, circuitry, and/or computer readable instructions of any suitable language (e.g., software stored onto a suitable memory and/or data storage device associated with the generator 111). Such systems can allow the user to set the sense (e.g. sensitivity) and ablation parameters (e.g. a number of electrodes to be used, ablation time, ablation temperature, impedance limits, nerve activity limits).

In some embodiments, the generator 111 can include a display 113 that displays inputs and/or outputs to and from the measuring and control systems, the temperature sensors 104, the electrodes 103, and/or the sensor 105. The display 113 can be any suitable display such as, but not limited to, an LCD screen or the like.

Figure 5:
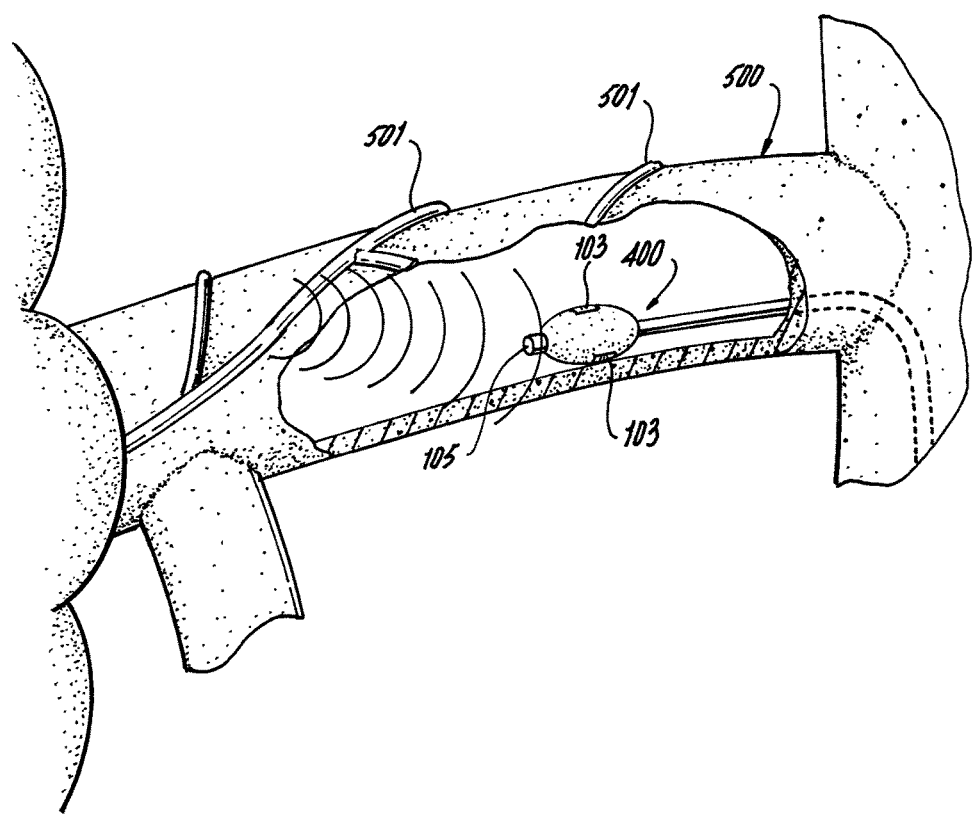
FIG. 5 is an in situ illustration of the embodiment of FIG. 4 disposed within a renal artery and sensing a signal from a renal sympathetic nerve.

In accordance with at least one aspect of this disclosure, referring to FIG. 5, a method can include the step of inserting a catheter body 101 into a renal artery, wherein the catheter body 101 includes a sensor 105 for sensing a condition associated with a sympathetic nerve 501 of a renal artery 500, as described herein. The method can further include sensing a condition associated with a sympathetic nerve 501 of a renal artery 500 as shown in situ in FIG. 5. In some embodiments, the method includes determining whether to ablate tissue (e.g., nerves 501) based on the sensed signals from the sensor 105. The method can also include ablating tissue (e.g., nerves 501) if the sympathetic nerves 501 are sensed to be over-active above a threshold activity. The method can also include stopping the application of electrosurgical energy if the nerves 501 are sensed to be within a suitable range of activity.

As disclosed herein, embodiments can be used to sense and measure the activity of the sympathetic nerve which can indicate if ablation is necessary due to over-activity of the sympathetic nervous system in the renal artery. To verify if an ablation procedure is performed successfully, embodiments of the present disclosure can also be used to measure nerve activity after ablation and verify that the nerves have ceased over-activity. If a nerve continues to be overactive after a period of ablation, a physician can perform ablation again and measure again until a sufficiently low nerve activity is observed.

Embodiments can facilitate location of the sympathetic nerves to ensure the ablation will be performed at the correct location in the renal artery 500. The location of the sympathetic nerve can be determined by sensing its electrical potential and/or other electrical phenomena associated with nerve activity, allowing nerve treatment to be performed, targeted, and focused while limiting the pain and long term risk of nerve damage to the patient. Embodiments used for location of the sympathetic nerves can also be used for mapping a sympathetic nerve system of a renal artery of a patient.

In some embodiments, the generator 111 can automate the process of determining nerve activity such that sensing can be done during ablation or intermittently between duty cycles of electrosurgical energy and then determine if proper nerve activity has been achieved. If the sensing module 115 has sensed proper nerve activity during ablation, the generator 111 can stop further electrosurgical energy from traveling to the electrodes 103 to prevent accidental over ablation. Otherwise, the generator 111 can continue to allow electrosurgical energy to flow to the electrodes for further ablation until proper nerve activity is achieved.

While the apparatus, systems, and methods of the subject disclosure have been shown and described with reference to preferred embodiments, those skilled in the art will readily appreciate that changes and/or modifications may be made thereto without departing from the spirit and scope of the subject disclosure.

What is claimed is:

1. A system for use in a renal denervation procedure, comprising:
    a) a catheter body having proximal and distal end portions, the distal end portion of the catheter body having a generally basket-shaped configuration that includes a pair of opposed arms joined at a distal tip section;
    b) a sensor configured to sense at least one of an electrical or magnetic condition of one or more nerves of the renal artery via electromagnetic radiation given off by the nerve cell, the sensor positioned on a distal tip of the distal tip section of the distal end portion of the catheter body, wherein the sensor is electrically coupled to a sensing module through a first set of wires;

c) at least one electrode disposed on each arm of the pair of opposed arms of the distal end portion of the catheter body for delivering energy to renal tissue, wherein the electrodes are electrically coupled to one another in parallel through a second set of wires discrete from the first set of wires;

d) an actuating rod extending through the catheter body for transitioning the distal end portion of the catheter body between a linear shape and the generally basket-shaped configuration; and e) at least one thermocouple is disposed on the distal end portion of the catheter body proximal to and discrete from the sensor for determining temperature at a desired location for regulating the plurality of electrodes during controlled ablation.

2. The system of claim 1, further including a catheter handle at the proximal end portion of the catheter body, the catheter handle including means for connecting the catheter handle to a generator that is configured to provide energy to the at least one electrode disposed on each arm of the pair of opposed arms of the distal end portion of the catheter body for ablation of the renal artery.

3. The system of claim 2, wherein the catheter handle includes a sliding switch connected to the actuating rod for moving the actuating rod within the catheter body.

4. The system of claim 2, further comprising a generator operatively connected to the catheter handle to provide energy to the at least one electrode disposed on each arm of the pair of opposed arms for ablation of the renal artery.

5. The system of claim 4, wherein the generator further includes the sensing module for receiving a signal from the sensor and determining a level of activity of the one or more nerves.

6. The system of claim 1, wherein an overall diameter of the catheter body is less than 5F.

7. A system for use in a renal denervation procedure, comprising:

a) a catheter body having proximal and distal end portions, the distal end portion of the catheter body having a generally basket-shaped configuration that includes a pair of opposed arms joined at a distal tip section;

b) a sensor configured to sense at least one of electrical amplitudes, electrical fields, magnetic fields, or electric potentials of one or more nerves of the renal artery, the sensor positioned on a distal tip of the distal tip section of the distal end portion of the catheter body, wherein the sensor is electrically coupled to a sensing module through a first set of wires;

c) at least one electrode disposed on each arm of the pair of opposed arms of the distal end portion of the catheter body for delivering energy to renal tissue, wherein the electrodes are electrically coupled to one another in parallel through a second set of wires discrete from the first set of wires;

d) an actuating rod extending through the catheter body for transitioning the distal end portion of the catheter body between a linear shape and the generally basket-shaped configuration; and e) at least one thermocouple disposed on the distal end portion of the catheter body proximal to and discrete from the sensor for determining temperature at a desired location for regulating the plurality of electrodes during controlled ablation.

* * * * *